(12) United States Patent
Paufique

(10) Patent No.: US 12,171,845 B2
(45) Date of Patent: Dec. 24, 2024

(54) USE OF A DRY FILM FOR COSMETIC TOPICAL APPLICATIONS

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

(21) Appl. No.: 17/040,143

(22) PCT Filed: Mar. 26, 2019

(86) PCT No.: PCT/EP2019/057527
§ 371 (c)(1),
(2) Date: Sep. 22, 2020

(87) PCT Pub. No.: WO2019/185597
PCT Pub. Date: Oct. 3, 2019

(65) Prior Publication Data
US 2021/0022966 A1    Jan. 28, 2021

(30) Foreign Application Priority Data
Mar. 26, 2018   (FR) ................. FR 1870340

(51) Int. Cl.
| | | |
|---|---|---|
| *A61K 8/02* | (2006.01) |
| *A61K 8/25* | (2006.01) |
| *A61K 8/34* | (2006.01) |
| *A61K 8/36* | (2006.01) |
| *A61K 8/44* | (2006.01) |
| *A61K 8/73* | (2006.01) |
| *A61Q 19/02* | (2006.01) |
| *A61Q 19/06* | (2006.01) |
| *A61Q 19/08* | (2006.01) |

(52) U.S. Cl.
CPC ............. *A61K 8/0208* (2013.01); *A61K 8/25* (2013.01); *A61K 8/342* (2013.01); *A61K 8/345* (2013.01); *A61K 8/36* (2013.01); *A61K 8/44* (2013.01); *A61K 8/731* (2013.01); *A61K 8/736* (2013.01); *A61K 8/737* (2013.01); *A61K 8/738* (2013.01); *A61Q 19/02* (2013.01); *A61Q 19/06* (2013.01); *A61Q 19/08* (2013.01); *A61K 2800/59* (2013.01)

(58) Field of Classification Search
CPC ...... A61K 8/0204; A61K 8/0208; A61K 8/19; A61K 8/25; A61K 8/26; A61K 8/342; A61K 8/345; A61K 8/36; A61K 8/44; A61K 8/72; A61K 8/73; A61K 8/731; A61K 8/736; A61K 8/737; A61K 8/738; A61K 2800/10; A61K 2800/59; A61Q 19/00; A61Q 19/008; A61Q 19/02; A61Q 19/06; A61Q 19/08
See application file for complete search history.

(56) References Cited

U.S. PATENT DOCUMENTS

| | | | | |
|---|---|---|---|---|
| 5,830,449 | A | * | 11/1998 | Afriat .................... A61Q 19/10 424/78.02 |
| 9,526,685 | B2 | | 12/2016 | Gombart et al. |
| 2013/0078209 | A1 | * | 3/2013 | Yu ........................... A61P 17/02 424/78.05 |
| 2014/0303135 | A1 | * | 10/2014 | Smith, III ............ A61K 8/4933 514/188 |
| 2017/0258698 | A1 | * | 9/2017 | Cabaret .................... A61K 8/26 |

FOREIGN PATENT DOCUMENTS

| | | | |
|---|---|---|---|
| EP | 0750905 A2 | 1/1997 | |
| EP | 0970681 A1 | 1/2000 | |
| EP | 2846764 A2 | 3/2015 | |
| FR | 3029103 A1 | 3/2016 | |
| WO | WO-2016083141 A1 * | 6/2016 | ........... A61K 8/0208 |

OTHER PUBLICATIONS

Tunc, et al., "Preparation and characterization of biodegradable methyl cellulose/montmorillonite nanocomposite films", Elsevier, Applied Clay Science, (2010), pp. 414-424, vol. 48.

* cited by examiner

*Primary Examiner* — Walter E Webb
*Assistant Examiner* — Amanda Michelle Petritsch
(74) *Attorney, Agent, or Firm* — Greer, Burns & Crain, Ltd.

(57) ABSTRACT

The present invention concerns the use of a dry film having a water activity of less than 0.6, for a non-therapeutic cosmetic topical treatment of the skin, which dry film comprises at least one polymer of natural origin, at least one mineral filler, at least one plasticizer and at least one surfactant. The dry film has a moisturizing and anti-sebum effect when applied to the skin. The invention also concerns a method of non-therapeutic cosmetic treatment of the skin.

17 Claims, No Drawings

USE OF A DRY FILM FOR COSMETIC TOPICAL APPLICATIONS

CROSS-REFERENCE TO RELATED APPLICATIONS

This application is the U.S. National phase application corresponding to PCT/EP2019/057527 which was assigned an international filing date of Mar. 26, 2019 and associated with publication WO 2019/185597 and which claims priority to French Patent Application FR 1870340 filed Mar. 26, 2018, the entire disclosures of which are expressly incorporated herein by reference.

TECHNICAL FIELD

The present invention relates to the use of a particular dry film, comprising or not comprising cosmetic active ingredient, for cosmetic applications. It also relates to a cosmetic method for the non-therapeutic treatment of skin, which method involves applying said dry film to healthy skin under certain conditions.

BACKGROUND

Today, there are different types of masks which are intended to take care of healthy skin, in particular the skin of the face: these include cream masks, mud masks, gel masks, and peel-off masks. All of these masks are chosen depending on the type of skin. But these masks contain little or no cosmetic active ingredients. There are also sheet masks, inspired by Asian beauty rituals, which contain an ultra-fine material impregnated with a lotion. Even though some of these masks claim the presence of active agents in their composition, there is no evidence as to the bioavailability of the active ingredient in the skin.

SUMMARY

One aim of the invention is therefore to provide a dry cosmetic film that is capable of acting on healthy skin and, when it contains a cosmetic active ingredient, of promoting the penetration of said active ingredient into the skin in a significant amount and/or more rapidly, i.e. to improve the dermal bioavailability of said active ingredient.

Orodispersible patches are known in the medical field for improving the bioavailability of therapeutic active ingredients. These medical devices have the specific feature of being instantly soluble upon contact with an aqueous medium and thus allowing the medicinal active ingredient to be taken directly in the mouth of patients, without water. This type of orodispersible patch, however, cannot be applied to the skin as a mask, as it will immediately disintegrate and is therefore not suitable.

In order to achieve the aim, the invention therefore proposes another solution, specifically the use of a particular dry film for topical cosmetic applications.

Dressings in film form already exist. One example is patent FR3029103, which discloses a soluble adhesive dressing in the form of a soluble film consisting of a natural polymer and a high mineral content, but which does not disclose and does not demonstrate any particular cosmetic application.

The film according to the invention has the particular feature of being in the form of a dry film, i.e. a form which is rarely developed in products to be applied to the skin, and of being able to be enriched with cosmetic active ingredients.

The constitution of this dry film very advantageously allows cosmetic effects to be obtained when applied to the skin without active ingredient, and, when said film does contain active ingredients, considerably promotes the bioavailability of said ingredients in the skin and therefore their functionality in the skin.

In particular, the invention relates to the use of a dry film having a water activity of less than 0.6, for a topical cosmetic treatment of healthy skin (i.e. non-therapeutic), which dry film comprises:
  at least one mineral filler, said mineral filler representing at least 5 wt. % of the dry film, and
  at least one polymer of natural origin, said polymer representing at least 15 wt. % of the dry film, and
  at least one plasticizer, said plasticizer representing at least 20 wt. % of the dry film, and
  at least one surfactant, said surfactant representing at least 0.1 wt. % of the dry film.

The particular useful dry film according to the invention can comprise other constituents and in particular at least one active ingredient.

Advantageously, a use of this kind can make it possible to obtain both an immediate effect and a medium- and long-term effect.

The invention also relates to a cosmetic method for the non-therapeutic treatment of skin, which involves applying a dry film having a water activity of less than 0.6 to the skin at least once for between 5 and 30 minutes, said dry film comprising:
  at least one mineral filler, said mineral filler representing at least 5 wt. % of the dry film, and
  at least one polymer of natural origin, said polymer representing at least 15 wt. % of the dry film, and
  at least one plasticizer, said plasticizer representing at least 20 wt. % of the dry film, and
  at least one surfactant, said surfactant representing at least 0.1 wt. % of the dry film.

Other features and advantages will become apparent from the detailed description of the invention which follows.

DETAILED DESCRIPTION

Definitions

"Polymer of natural origin" or "biopolymer," within the meaning of the invention, is understood to mean polymers derived from natural raw materials, as opposed to synthetic polymers which are obtained by chemical synthesis.

"Film," within the meaning of the invention, is understood to mean a cosmetic product which is applied momentarily to the skin and which is removed after a certain application time, and which exhibits a cosmetic or dermocosmetic effect. It may be a face mask, for example.

"Cosmetic active ingredient" or "cosmetic active agent" or "active ingredient" or "active agent," within the meaning of the invention, is understood to mean one or more molecules which are cosmetically effective when applied to the skin.

"Compatible with a topical cosmetic application," within the meaning of the invention, is understood to mean that the agent must not be harmful to the skin and trigger undesirable effects as a result of its presence in the composition. It is therefore a cosmetically acceptable product as defined in European Regulation No. 1223/2009, which relates to cosmetic products.

"Non-therapeutic cosmetic treatment of the skin," within the meaning of the invention, is understood to mean a cosmetic treatment on healthy skin.

"Soothing cosmetic treatment," within the meaning of the invention, is understood to mean a cosmetic treatment which relieves itching, discomfort and irritations of the skin. It is therefore a treatment for comfort which does not aim to treat a skin disease by restoring health.

"Water content" of the dry film is understood to mean the quantity of liquid water contained in the film (weight ratio of water to the total weight of the film).

The invention relates to the use of a dry and soluble film having a water activity of less than 0.6, for a non-therapeutic topical cosmetic treatment of healthy skin, which dry film comprises:
  at least one mineral filler, and
  at least one polymer of natural origin, and
  at least one plasticizer, and
  at least one surfactant.

In particular, the invention relates to the use of a dry and soluble film of this kind for one or more of the following specific cosmetic applications:
  moisturizing
  smoothing
  improving the radiance of the complexion
  anti-sebum
  anti-wrinkle
  anti-aging
  depigmenting
  anti-dark circles
  anti-under-eye puffiness
  anti-skin imperfections
  soothing
  anti-cellulite.

The use according to the invention preferably relates to at least one use for a moisturizing and/or anti-sebum effect and optionally one or more other specific cosmetic applications, in particular selected from those mentioned above.

The dry and soluble useful film according to the invention can exhibit these cosmetic effects without containing an active ingredient, but these effects can be reinforced by the presence of one or more cosmetic active ingredients in the film. This is because the specific constitution and characteristics of the dry film make it possible to promote the transdermal bioavailability of the active ingredients in significant quantities. Due to its constitution and its characteristic of a dry film having a water activity of less than 0.6, said film has special mechanical properties which ensure strength and flexibility for optimal application to the skin and easy and simple use.

The film preferably has a water activity of less than 0.6. This parameter, well known to a person skilled in the art, makes it possible to identify the availability of water in the material. It can be measured by means of a device known as an AW meter, such as a LabSwift-AW meter. The value is unitless and between 0 and 1.

The water content of the dry and soluble film of which the cosmetic use is the subject of the invention is preferably less than 6 wt. % of the total weight of the dry film. This parameter is different from the water activity and is measured by successive weighings before and after drying in an oven.

The solubility of the dry film of which the cosmetic use is the subject of the invention is preferably determined as follows: a round of film having a diameter of 3.5 cm is placed in 20 ml of water at 25° C. while stirring at 200 rpm. A film is considered to be soluble within the meaning of the invention when it is completely dissolved in less than an hour.

The film is preferably:
  non-sticky and non-brittle,
  strong and flexible.

According to the invention, the dry film, advantageously when applied to the skin:
  has a moisturizing effect,
  has an anti-sebum effect,
  has a smoothing effect,
  has a radiant effect on the complexion,
  allows high bioavailability of the active ingredient(s) possibly present in the film, and consequently promotes their transdermal penetration into the skin,
  is easy to apply and remove from the skin.

This is the case without active ingredient or with any cosmetic active ingredient. It can also exhibit additional cosmetic effects depending on the cosmetic effectiveness of the active ingredient(s) present in the film.

The invention therefore also relates to the use of a film on skin to promote the transdermal penetration of the cosmetic active ingredient(s) present in the film. This is because, when applied to the skin, the film according to the invention allows the active ingredients which it contains to have greater bioavailability in the skin by comparison with that obtained with the cosmetic or dermocosmetic masks of the prior art.

The dry and soluble film according to the invention can also be used in particular for:
  an anti-wrinkle effect, and/or
  to improve or standardize the radiance of the skin, and/or
  to lighten the color of the skin and/or
  to decrease the color of age spots, and/or
  to improve cutaneous microcirculation, and/or
  to reduce the color of dark circles, and/or
  to decrease puffiness, and/or
  to smooth skin imperfections, and/or
  to decrease the size of the pores in the skin, and/or
  to reduce the imperfections of acne-prone skin, and/or
  to improve the barrier effect of the skin, and/or
  to improve the comfort of atopic skin, and/or
  to improve the comfort of sensitive or reactive skin, and/or
  to decrease the signs of skin irritation, and/or
  to decrease the signs of skin aging, and/or
  to decrease the cellulite state of the skin, and/or
  to improve the skin appearance of cellulite skin.

The dry and soluble film used according to the invention preferably comprises from 0.5 to 25% of at least one cosmetic active ingredient. The cosmetic active ingredient(s) can be selected from known or unknown cosmetic active ingredients, and in particular said film comprises at least one active ingredient selected from cosmetic active ingredients which moisturize and/or smooth and/or improve the radiance of the complexion and/or have an anti-sebum and/or anti-wrinkle and/or anti-aging and/or depigmenting and/or anti-dark circles and/or anti-under-eye puffiness and/or anti-skin imperfections and/or soothing and/or anti-cellulite effect.

The use can be for an immediate and optionally single effect, or for a cure effect.

The dry and soluble film of which the cosmetic use is the subject of the invention preferably comprises at least one mineral filler which is selected from kaolin, talc, sodium or calcium montmorillonite, mica, illite, perlite, diatom, potassium salts, sodium salts or calcium salts, and mixtures thereof. The mineral filler can represent at least 5 wt. % of the dry film, preferably between 5% and 75%. These mineral fillers are not in the form of nanoparticles, and have not been chemically modified.

The polymer(s) of natural origin is/are selected from polymers extracted from plants or algae or microorganisms. Said polymer is preferably a polysaccharide of natural origin, and the polymer(s) of natural origin present in the dry useful film according to the invention are preferably selected from pullulan, cellulose, chitosan, acacia gum, guar gum, tara gum, gellan gum, konjac gum, xanthan gum, pectin, maltodextrin, cyclodextrins, polysaccharides, carrageenans, and mixtures thereof. The content of polymers of natural origin in the dry film is preferably greater than 15 wt. % of the dry film, and preferably between 15 and 75 wt. % of the dry film.

The polymers of natural origin are preferably soluble in water.

The dry and soluble film as described above also comprises other constituents and in particular:
- at least one surfactant which is compatible with a topical cosmetic application and represents less than 10 wt. % of the dry matter of the film, preferably less than 2 wt. % of dry matter of the film, and
- at least one plasticizing agent which is compatible with a topical cosmetic application and preferably selected from urea, glycerol, esters and ethers of glycerol, monosaccharides, sorbitol, sucrose, amino acids, glycols such as butylene glycol or propylene glycol, fatty alcohols, salts, lactate esters and ethers, and mixtures thereof, the plasticizing agent(s) being present between 20 and 80 wt. % relative to the dry matter weight of the film. The plasticizer is preferably soluble in water.

However, the dry and soluble film does not comprise hydrophobic polymers such as polyisobutylenes, vinyl ether polymer or polysiloxanes.

In the context of the use of the dry and soluble film as described above, the invention is also specifically aimed at a cosmetic method for the non-therapeutic treatment of skin, which involves applying a useful film according to the invention to the skin at least once for between 5 and 30 minutes, preferably for an effect which moisturizes and/or smooths and/or improves the radiance of the complexion and/or for an anti-sebum and/or anti-wrinkle and/or anti-aging and/or depigmenting and/or anti-dark circles and/or anti-under-eye puffiness and/or anti-skin imperfections and/or soothing and/or anti-cellulite effect. The skin is preferably dampened before the film is applied.

A particularly suitable application time is between 10 and 30 minutes.

The film can be applied to the face for use as a mask, for example, but can also be applied to any other part of the body such as regions which have cellulite or imperfections. The film must therefore have mechanical properties which allow it to match any shape of the face or body. It must be flexible in order to be easily applied to the face or body. It must be strong so as to not tear during handling when being placed on the skin. It must be resilient to adapt to all shapes (hollows, reliefs) of the skin.

In order to obtain a cumulative effect, i.e. a cure effect, it is preferable to apply the film to the skin at least twice a week.

The invention will now be illustrated by examples of dry films and test results demonstrating the cosmetic effectiveness of said films.

EXAMPLES

A number of examples of films are presented.

Example 1

This example presents various films which either do not comprise active ingredient or comprise one or two active ingredients.

Film A does not contain an active ingredient.

Film B contains an active ingredient, namely di- and tripeptides. The compositions of the films are set out below:

|  | % of the dry matter | |
| --- | --- | --- |
| Film | 1A | 1B |
| Mineral filler | 28.6% | 28.3% |
| Natural polymers: carrageenan, cellulose, guar gum | 18.9% | 18.8% |
| Plasticizer | 52.0% | 51.5% |
| Surfactant | 0.5% | 0.5% |
| Active ingredient | 0% | 0.9% |

Example 2

This example presents various films which either do not comprise active ingredient or comprise one or two active ingredients.

Film A does not contain an active ingredient.

Film B contains an active ingredient, namely glucose-fructose and galactoxylan oligosaccharides.

Film C contains an active ingredient, namely peptides.

Film D contains an active ingredient, namely sulfated polygalactomannans and galactans.

The compositions of the films are set out below:

|  | % of the dry matter | | | |
| --- | --- | --- | --- | --- |
| Film | 2A | 2B | 2C | 2D |
| Mineral filler | 31.0% | 30.1% | 30.5% | 30.6% |
| Natural polymers Cellulose, gellan gum | 20.0% | 19.4% | 19.7% | 19.7% |
| Plasticizer | 48.1% | 46.6% | 47.2% | 47.5% |
| Surfactant | 0.9% | 0.9% | 0.9% | 0.9% |
| Active ingredient(s) | 0% | 3.0% | 1.7% | 1.3% |

Example 3

This film contains an active ingredient, namely glucose-fructose oligosaccharides. The composition of said film is set out below:

|  | % of the dry matter |
| --- | --- |
| Mineral filler | 11.8% |
| Natural polymers Carrageenan, pullulan | 47.4% |
| Plasticizer | 35.5% |
| Surfactant | 1.2% |
| Active ingredient | 4.1% |

Example 4

This film contains an active ingredient, namely glucose-fructose oligosaccharides. The composition of said film is set out below:

|  | % of the dry matter |
| --- | --- |
| Mineral filler | 14.8% |
| Natural polymers | 34.4% |
| Konjac gum, pectin |  |
| Plasticizer | 44.3% |
| Surfactant | 1.5% |
| Active ingredient | 5.1% |

Example 5

This film contains an active ingredient, namely glucose-fructose oligosaccharides. The composition of said film is set out below:

|  | % of the dry matter |
| --- | --- |
| Mineral filler | 10.1% |
| Natural polymers | 35.2% |
| Pectin, xanthan gum |  |
| Plasticizer | 50.3% |
| Surfactant | 1.0% |
| Active ingredient | 3.5% |

Example 6

This example presents various films which either do not comprise active ingredient or comprise one or two active ingredients.

Film A does not contain an active ingredient.

Film B contains an active ingredient, namely di- and tripeptides.

Film C contains an active ingredient, namely polyphenolic acids.

The compositions of the films are set out below:

|  | % of the dry matter | | |
| --- | --- | --- | --- |
|  | 6A | 6B | 6C |
| Mineral filler | 35.0% | 34.5% | 34.8% |
| Natural polymers: guar and acacia gums | 23.5% | 23.1% | 23.2% |
| Plasticizers | 40.8% | 40.3% | 40.6% |
| Surfactant | 0.6% | 0.6% | 0.6% |
| Active ingredient | 0% | 1.2% | 0.5% |

Example 7

This film contains an active ingredient, namely glucose-fructose oligosaccharides. The composition of said film is set out below:

|  | % of the dry matter |
| --- | --- |
| Mineral filler | 9.0% |
| Natural polymers | 36.0% |
| Konjac and guar gums |  |
| Plasticizer | 51.0% |
| Surfactant | 0.9% |
| Active ingredient | 3.1% |

Example 8

The film of this example contains two active ingredients, namely galactoxylan and glucose-fructose oligosaccharides. The composition of said film is set out below:

|  | % of the dry matter |
| --- | --- |
| Mineral filler | 38.0% |
| Natural polymers | 15.6% |
| Carrageenan, acacia gum |  |
| Plasticizers | 34.2% |
| Surfactant | 9.7% |
| Active ingredients | 2.5% |

Example 9

This film contains two active ingredients, namely galactoxylan and glucose-fructose oligosaccharides. The composition of said film is set out below:

|  | % of the dry matter |
| --- | --- |
| Mineral filler | 38.0% |
| Natural polymers | 15.6% |
| Carrageenan, acacia gum |  |
| Plasticizers | 11.8% |
| Surfactant | 9.7% |
| Active ingredients | 24.9% |

Example 10

This example film contains two active ingredients, namely peptides and glucose-fructose oligosaccharides. The composition of said film is set out below:

|  | % of the dry matter |
| --- | --- |
| Mineral filler | 14.7% |
| Natural polymers: guar gum, kappa-carrageenans, cellulose | 32.1% |
| Plasticizer | 50.6% |
| Surfactant | 0.7% |
| Active ingredients | 1.4% |

Example 11

This example presents various films which either do not comprise active ingredient or comprise one or two active ingredients.

Film A does not contain an active ingredient.

Film B contains two active ingredients, namely galactoxylan and glucose-fructose oligosaccharides.

Film C contains an active ingredient, namely a glucose, fructose and galacturonic acid oligosaccharide.

Film D contains an active ingredient, namely galactomannan oligosaccharides.

Film E contains an active ingredient, namely mannan polysaccharides.

The compositions of the films are set out below:

|  | % of the dry matter | | | | |
| --- | --- | --- | --- | --- | --- |
|  | 11A | 11B | 11C | 11D | 11E |
| Mineral filler | 11.0% | 10.6% | 10.9% | 10.8% | 10.9% |
| Natural polymers | 40.6% | 39.2% | 40.3% | 39.9% | 40.0% |
| Pectin, pullulan | | | | | |
| Plasticizers | 47.4% | 45.8% | 47.2% | 46.6% | 46.9% |
| Surfactant | 1.0% | 1.0% | 1.0% | 1.0% | 1.0% |
| Active ingredient(s) | 0% | 3.4% | 0.6% | 1.7% | 1.2% |

Example 12

This film contains two active ingredients, namely galactoxylan and glucose-fructose oligosaccharides. The composition of said film is set out below:

|  | % of the dry matter |
| --- | --- |
| Mineral filler | 71.8% |
| Natural polymers | 15.0% |
| Acacia gum, carrageenan | |
| Plasticizers | 12.0% |
| Surfactant | 1.2% |
| Active ingredients | 0% |

Example 13

This film does not contain any active ingredient. The composition of said film is set out below:

|  | % of the dry matter |
| --- | --- |
| Mineral filler | 50.8% |
| Natural polymers | 16.2% |
| Cellulose, acacia gum, tamarind gum | |
| Plasticizers | 32.3% |
| Surfactant | 0.7% |
| Active ingredient | 0% |

Example 14

This film does not contain any active ingredient. The composition of said film is set out below:

|  | % of the dry matter |
| --- | --- |
| Mineral filler | 6.4% |
| Natural polymers | 70.2% |
| Carrageenan, konjac gum | |
| Plasticizers | 22.4% |
| Surfactant | 1.0% |
| Active ingredient | 0% |

Example 15

This film does not contain any active ingredient. The composition of said film is set out below:

|  | % of the dry matter |
| --- | --- |
| Mineral filler | 7.5% |
| Natural polymers | 52.2% |
| Plasticizers | 39.2% |
| Surfactant | 1.1% |
| Active ingredient | 0% |

Example 16

This example film contains two active ingredients, namely peptides and glucose-fructose oligosaccharides. The composition of said film is set out below:

|  | % of the dry matter |
| --- | --- |
| Mineral filler | 15.8% |
| Natural polymers: | 27.0% |
| guar gum, carrageenan, cellulose | |
| Plasticizer | 55.1% |
| Surfactant | 0.6% |
| Active ingredients | 1.5% |

Example 17

This example film contains two active ingredients, namely polyphenols and oligofructosans. The composition of said film is set out below:

|  | % of the dry matter |
| --- | --- |
| Mineral filler | 16.9% |
| Natural polymers: | 28.8% |
| guar gum, carrageenan, cellulose | |
| Plasticizer | 50.6% |
| Surfactant | 0.6% |
| Active ingredients | 3.1% |

Examples of Masks of the Prior Art

The formulas of these masks of the prior art are also produced:

| Formula 1: | | | |
| --- | --- | --- | --- |
| Formula | Trade name | Chemical name | Formula content (%) |
| Cream mask | Montanov 202 | behenyl alcohol/ arachidyl glucoside/ arachidyl alcohol | 5% |
|  | Montanov 68 | Cetearyl alcohol/ cetearyl glucoside | 5% |
|  | Lanol 99 | Isonyl isononoate | 10% |
|  | Lanol 1688 | Cetearyl ethylhexanoate | 5% |
|  | Active agent 1 | Water of the active agent 1 | — |
|  |  | Glucose-fructose oligosaccharides | 0.14% |

-continued

Formula 1:

| Formula | Trade name | Chemical name | Formula content (%) |
|---|---|---|---|
| | Active agent 2 | Water of the active agent 2 | — |
| | | Galactoxylan oligosaccharides | 0.38% |
| | propylene glycol | Propylene glycol | 3.5% |
| | preservative | Phenonip XB | 1% |
| | Satialgine US 551 | Sodium alginate | 0.1% |
| | Water | Water | To make up to 100% |

Formula 2:

| Formula | Trade name | Chemical name | Formula content (%) |
|---|---|---|---|
| Hydrogel mask | carrageenan | carrageenan | 2.0% |
| | Active agent 1 | Water of the active agent 1 | — |
| | | Glucose-fructose oligosaccharides | 0.14% |
| | Active agent 2 | Water of the active agent 2 | — |
| | | Galactoxylan oligosaccharides | 0.38% |
| | Preservative | Phenonip XB | 0.7% |
| | Water | Water | To make up to 100% |

Formula 3:

| Formula | Trade name | Chemical name | Formula content (%) |
|---|---|---|---|
| Sheet mask + Lotion | Glycerin | Glycerin | 2% |
| | butylene glycol | Butylene glycol | 2% |
| | propylene glycol | Propylene glycol | 1% |
| | Active agent 1 | Water of the active agent 1 | — |
| | | Glucose-fructose oligosaccharides | 0.14% |
| | Active agent 2 | Water of the active agent 2 | — |
| | | Galactoxylan oligosaccharides | 0.38% |
| | Preservative | Phenonip XB | 1% |
| | Water | Water | To make up to 100% |

Mechanical Properties of the Films

The Young's modulus of the films according to the invention of a number aforementioned examples and those corresponding to the prior art (FR3029103, films denoted D, E and F) were measured on a TAXplus texture analyzer.

The physical characteristics obtained by the TAXplus texture analyzer are as follows:
the breaking force which is the maximum force necessary to break the film
conventional stress (MPa)=(breaking force)/(work surface)
work surface (mm2)=(width−6 mm)/(thickness)
relative elongation=(elongation)/(length−34)

Young's modulus (MPa)=(conventional stress)/(relative elongation)

Young's modulus is a measure which therefore makes the characteristics of the films redundant. The lower the value, the more flexible the film.

Energy corresponds to the energy required to break the film.

Elongation is the film's ability to stretch without breaking.

The results are shown in the table below.

| | Young's Modulus (MPa) | Energy (N sec) | Elongation (mm) |
|---|---|---|---|
| Example 4 | 1.9 | 327 | 24.8 |
| Example 2 | 3.8 | 86.5 | 33 |
| Example 11 | 3.9 | 80 | 20 |
| Example 1 | 5.4 | 44 | 20 |
| Example 10 | 1.6 | 26 | 32 |
| Example 6 | 3.6 | 44 | 30 |
| Film D | 7.3 | 4 | 4.5 |
| Film E | 34.6 | 18.8 | 5 |
| Film F | 37.8 | 12.1 | 3.6 |

Films D, E and F are films corresponding to those described in FR3029103.

Film D is the most flexible of the films according to the prior art (the Young's modulus gives a value of 7.3, which is much lower than that of films E and F), but it breaks more quickly (energy required to break=4 N sec) and is not very resilient (elongation of 4.5 mm).

Examples 1, 2, 4, 6, 10 and 11 of the present invention are all characterized by a Young's modulus lower than that of the films of the prior art. They are therefore more flexible. However, the energy required to break all of them is higher than that according to the prior art. They are therefore stronger. Finally, their elongation without breaking is higher than for the films of the prior art. They are therefore more extendable.

Tests Demonstrating the Cosmetic Effectiveness of the Dry Film

Tests—Demonstration of the Bioavailability of the Active Ingredients in the Films In order to evaluate the bioavailability properties of the active ingredients in the films, a number of formulas have been produced.

The ability of a film to make an active agent available in the skin was studied ex-vivo after depositing the tested film containing the active agent on the surface of a pig ear skin. This study is based on the standard for transcutaneous penetration, OECD 428.

The film containing the active agent of which the bioavailability is being studied is deposited on the skin for 10 to 20 minutes. After 10 to 20 minutes of contact, the film is removed and the molecules present on the surface of the skin are eliminated. The layers of the stratum corneum of the skin are then collected and the active agent present in these layers is extracted and quantified; this corresponds to the content of the active agent present in the stratum corneum.

Each test is carried out 3 times on 6 different skins.

The dosage of the active agent in the samples is carried out according to a method adapted to the nature of the active agent being tested, such as by fluorometry, chromatography, or any other analytical method suitable for the dosage of the selected active agent.

The results are expressed as a percentage of active agent present in the stratum corneum relative to the quantity of active agent deposited on the skin.

A person skilled in the art considers that a film allows bioavailability of an active ingredient when the bioavailability thereof in the stratum corneum is at least 5%.

For the purposes of comparing with standard formulas on the market, the three classic formulas of masks of the prior art presented in the examples were selected in order to study the bioavailability of the active ingredients which they contain; these are a cream mask, a hydrogel mask and a fabric mask+lotion.

The average of the percentages of availability of an active agent in the stratum corneum after the masks of the prior art have been applied to the skin for 10 to 20 minutes are as follows:

|  | % availability of the active agent (glucose-fructose oligosaccharides) in the stratum corneum |
|---|---|
| Cream mask (formula 1) | 2.7% ± 0.5 |
| Hydrogel mask (formula 2) | 2.2% ± 1.1 |
| Sheet mask + lotion (formula 3) | 3.0% ± 1.0 |

The different formulas of the masks on the market allow low bioavailability of the active agent in the stratum corneum. Moreover, no variation is observed between the different formulas, whether of the cream mask, sheet mask+ lotion or hydrogel mask type.

Different dry films according to the invention were tested. The formulas have been described previously.

| Example film | % availability of the active agent in the stratum corneum |
|---|---|
| Example 8 | 9.4% ± 2.1 |
| Example 12 | 10.0% ± 4.0 |
| Example 3 | 11.2% ± 3.2 |
| Example 4 | 12.4% ± 4.5 |
| Example 5 | 18.6% ± 7.4 |
| Example 7 | 10.3% ± 3.6 |
| Example 2B | 11.4% ± 2.6 |
| Example 11B | 10.0% ± 2.7 |
| Example 10 | 9.8% ± 3.5 |
| Example 1B | 15.4% ± 3.8 |
| Example 16 | 16.0% ± 4.2 |

It can be seen that all of these films according to the invention have the ability to make the active ingredient they contain available in the stratum corneum.

| Example film | % availability of the active agent in the stratum corneum |
|---|---|
| Example 11B Containing glucose-fructose and galactoxylan oligosaccharides | 10.0% ± 2.7 |
| Example 11C containing glucose, fructose and galacturonic acid oligosaccharides | 8.2% ± 2.2 |
| Example 11D containing galactomannan oligosaccharides | 11.5% ± 1.2 |
| Example 11E containing mannans | 10.2% ± 3.5 |

It is noted that the nature of the active agent has little influence on the availability of the active agent in the stratum corneum. All of the active agents are bioavailable in the skin when applied by the film.

Tests—Demonstration of the Cosmetic Effectiveness of the Films

The functionality on the skin of different films containing or not containing different active ingredients, i.e. the performances in terms of cosmetic effectiveness of the films, was evaluated on volunteers. The cosmetic evaluation of the films focused on the effect of moisturizing or smoothing or improving the radiance or lightening/depigmenting or the anti-seborrheic or anti-aging effect. The effects were also studied immediately, after the application of a single film, or over the long term after a cure treatment of a plurality of films.

The studies were carried out successively to the use of the films.

The volunteers applied the film to the face or part of the face for 10 to 20 minutes. The moisturizing, smoothing, complexion radiance, anti-seborrhea and anti-wrinkle effects were evaluated immediately after a single film to evaluate the immediate effect, and/or after the application of 8 films spread over 28 days to evaluate the long-term effect.

For the different studies the selection criteria were as follows:
age between 25 and 65 years old
regular user of face masks (minimum 1/month)

Additional criteria relating to the skin of the volunteers were considered depending on the nature of the study.

Evaluation of the Moisturizing Effect

This study involves evaluating the immediate moisturizing effect of the film not containing or containing an active ingredient. The rate of hydration was measured on the forehead using a MoistureMeter-D® from Delfin Technologies.

The MoistureMeter D° generates a high frequency electromagnetic wave that is sent by a probe to the skin. The reflected electromagnetic wave is recorded, and a dielectric constant proportional to the water content of the tissue measured is thus obtained.

The higher the value of this constant, the greater the water content of the tissue. The probe used to carry out the measurements is the XS5 probe which mainly measures the water content of the epidermis at the effective measuring depth of 0.5 mm.

12 to 21 volunteers applied one of the films to the face for 10 minutes. The measurements were taken before and after removal of the film.

The results are shown in the following table:

|  |  | Skin hydration rate |
|---|---|---|
| Without active ingredient | Example 2A | +5.6% |
|  | Example 6A | +6.1% |
|  | Example 1A | +5.3% |
| With active ingredient(s) | Example 12 containing glucofructan oligosaccharides | +5.5% |

-continued

| | Skin hydration rate |
|---|---|
| Example 6C containing polyphenolic acids | +8.9% |
| Example 6B containing di- and tripeptides | +7.4% |
| Example 1B containing di- and tripeptides | +5.9% |
| Example 10 containing peptides and glucose-fructose oligosaccharides | +6.9% |

After using a dry film that does or does not contain active ingredient, the skin hydration rate is significantly increased. As a result of applying the film for 10 minutes, the superficial layers of the skin were hydrated.

Evaluation of the Anti-Seborrhea Effect

The anti-seborrhea effect is evaluated by measuring the level of sebum on the surface of the skin. The sebum level was measured on the forehead before and after application of the film. The measurements were carried out using an MPA 580® handset. The MPA580® allows direct measurement of sebaceous secretion. The plastics film contained in a cartridge is translucent and matte (such as frosted glass). Upon contact with sebum, this film becomes transparent depending on the amount of sebum located on the surface of the skin. The sebum level is determined by inserting the head of the cartridge into the MPA580® handset. A cell then analyzes the transparency of the film. The results are displayed in μg of sebum/cm$^2$ of skin.

The measurements were taken before applying the film and 10 minutes after removing the film. The different films were tested by 11 to 21 volunteers who have a sebum level greater than 150.

The results are as follows:

| | | Sebum level |
|---|---|---|
| Without active ingredient | Example 2A | −26.4% |
| | Example 6A | −37.5% |
| | Example 1A | −18.6% |
| With active ingredient(s) | Example 9 | −88.9% |
| | Example 11D containing polyphenolic acids | −22.0% |
| | Example 11C containing di- and tripeptides | −20.8% |
| | Example 1B containing di- and tripeptides | −20.5% |
| | Example 2D containing peptides | −22.0% |
| | Example 10 containing peptides and glucose-fructose oligosaccharides | −29.8% |

As a result of applying a dry film for 10 minutes, the production of sebum is reduced significantly, regardless of whether or not the film contains an active ingredient.

The users noted that the application of such films significantly limits the shiny appearance of the skin that is characteristic of people with oily skin (−44%), and tends to tighten the pore size by 12%.

Evaluation of the Smoothing Effect

The smoothing effect was evaluated by analyzing the cutaneous microrelief of crow's feet by means of fringe projection, using a device dedicated to 3D measurement of cutaneous relief (Eotech). This system (DermaTOP 1303) comprises a measurement sensor which combines a light fringe projector and a high-resolution CCD camera linked to Optocat acquisition software (Eotech).

A system for repositioning the head of the volunteer according to the 3 axes of movement makes it possible to find the same measurement zone at different times in the study.

The effect of the film is measured in a region of interest automatically cut out from the original acquisition.

The microrelief of the skin is studied using the 3D roughness parameter (Sa) which represents the arithmetic mean of surface roughness.

The software used is OPTOCAT, EOTECH software. A decrease in these different parameters is characteristic of a smoothing of the studied surface.

The volunteers were asked to subjectively evaluate this effect using closed questions with the answers (agree, tend to agree, tend to disagree and disagree):
this film provides instant smoothing;
this film refines the texture of the skin;
this film provides immediate smoothing.

a. Immediate Effect

This first study involves evaluating the immediate effect of the film. 12 to 20 volunteers applied the film to the face for 20 minutes. The measurements were taken before and 30 minutes after removing the film.

The results are shown in the following table:

| | | Smoothing effect (reduction of the roughness parameter Sa) | Subjective evaluation from the volunteers |
|---|---|---|---|
| With active ingredient(s) | Example 6B | +1.2% | 69% of volunteers consider that this film provides instant smoothing |
| Without active ingredient | Example 2A | +5.6% | 88% of volunteers consider that this film provides instant smoothing |

After using a film, the Sa parameter which is characteristic of the roughness of the cutaneous microrelief is reduced. As a result of applying the film for 20 minutes, the cutaneous microrelief of the volunteers is smoothed. The film provides instant smoothing and refines the skin texture.

b. Long-Term Effect

This study consists in evaluating the long-term effect of the film. 12 to 20 volunteers used 8 films in 28 days. Each film was applied to the face for 20 minutes. The measurements were taken before the first film and the day after the eighth film.

The results are as follows:

| | Smoothing effect (reduction of the roughness parameter Sa) |
|---|---|
| Cure example 2A | +7.1% |

After a cure treatment of 8 smoothing films, the parameter Sa which is characteristic of the roughness of the cutaneous microrelief is reduced by 7.1%. As a result of the cure treatment of 8 films, the cutaneous microrelief of the volunteers is lastingly smoothed.

According to 88% of volunteers, the film smooths their skin in a lasting way and limits skin imperfections.

Evaluation of the Radiant Effect on the Complexion

The radiance of the complexion was evaluated blindly by two experts previously trained to judge different parameters that are representative of the radiance of the complexion.

The evaluation is carried out on the basis of score scales (from 1 to 10) and the following parameters have been identified:

- The radiance of the skin is characteristic of a radiant complexion. The greater the intensity of light catching on the prominent regions of the face, the more luminous the skin.
- The light pink color characterizes a radiant complexion. The more rosy the complexion, the more it is perceived as fresh.
- The parameter of olive color is representative of the healthy glow effect; if the olive color decreases, the healthy glow effect is greater.
- The general perception of healthy glow reflects the homogeneity of color and its spatial distribution over the entire face.

These different parameters are evaluated in the regions of the cheekbones, forehead, chin and eyes.

The volunteers were asked to subjectively evaluate this effect using closed questions with the answers (agree, tend to agree, tend to disagree and disagree):

this film provides a boost of radiance;

this film revives the complexion.

a. Immediate Effect

This first study involves evaluating the immediate effect of the film comprising or not comprising active ingredient. 15 to 20 volunteers applied the film to the face for 20 minutes.

The measurements were taken before and 30 minutes after removing the film.

The results are shown in the following table:

|  |  | Radiance of the skin | Appearance of a healthy glow | Subjective evaluation from the |
| --- | --- | --- | --- | --- |
| With active ingredient(s) | Example 11B | +8.9% | +3.3% | 81% |
| Without active ingredient | Example 2A | +7.8% | +4.9% | 69% |

After using a film, the radiance of the skin of the volunteers is significantly improved up to 8.9%, and the healthy glow effect up to 4.9%.

As a result of applying the film for 20 minutes, the film improves the healthy glow effect and the radiance of the skin of the volunteers.

According to at least 69% of the volunteers, the film provides an immediate boost of radiance and revives the radiance of the complexion.

b. Long-Term Effect

This study consists in evaluating the long-term effect of the film. 15 to 20 volunteers used 8 films in 28 days. Each film was applied to the face for 20 minutes. The measurements were taken before the first film and the day after the eighth film.

The results are as follows:

|  | Appearance of a healthy glow | Radiant complexion (pink color) | Dull complexion (olive color) |
| --- | --- | --- | --- |
| Cure example 2A | +6.6% | +13.8% | −10.3% |

After a cure treatment of 8 films, the healthy glow effect of the volunteers is significantly improved by 6.6%, the radiant complexion improved by 13.8% and the dull complexion decreased by 10.3%.

The cure treatment of 8 films helped to improve the healthy glow effect and radiant complexion and reduce the dull complexion of the volunteers' skin.

According to 81% of volunteers, the cure treatment of 8 films gives permanent radiance to their skin and 94% of the volunteers indicated that the cure treatment of 8 films makes their skin more homogeneous.

Evaluation of the Immediate Anti-Wrinkle Effect

The immediate anti-wrinkle effect was evaluated by analyzing the depth of the main wrinkle on the crow's feet. Standardized photographs of the face were taken under reproducible lighting conditions using a VISIA-CR system (Canfield). Displaying the initial images at the different measurement times and using a marking film make it possible to ensure the correct repositioning of the subjects at different times in the study.

A panel composed of 3 people then evaluated the stage of wrinkles of the crow's feet in each photo on a previously defined score scale. Each of the photos had been previously cut, coded and randomized in order to carry out this completely blind evaluation.

The wrinkles of the crow's feet were evaluated according to the following recommendations: evaluate the depth of the main wrinkle, disregard the number of wrinkles, disregard the width of the wrinkles, and disregard any scars. The volunteers were asked to evaluate the stage of the wrinkles of their crow's feet using the scale above by looking at themselves in a mirror. This evaluation was carried out before and after using the film.

The study involves evaluating the immediate effect of the film for its immediate anti-wrinkle effect. 12 to 20 volunteers applied the film to the face for 20 minutes. Self-assessments were performed before and 30 minutes after removing the film.

The results are shown in the following table:

|  | Stage of crow's feet wrinkles according to the experts | Volunteers' self-assessment of the stage of wrinkles |
| --- | --- | --- |
| Example 2D containing sulfated galactomannan and galactan polysaccharides | −11.5% | −16.7% |

After using a film, the experts, like the volunteers, assessed that the wrinkles of the crow's feet were smoothed out. The stage of wrinkles decreased significantly.

The volunteers also indicated that the film makes the skin smoother, more hydrated and softer for 92% of the volunteers. The film lifts for 75% of the volunteers. For 92% of the volunteers, the film reduced wrinkles of the eye contour and faded fine lines and wrinkles.

The invention claimed is:

1. A method for a topical cosmetic treatment of healthy skin, the method comprising:
   a) applying for at least 5 minutes to the facial and/or body skin a dry, soluble and flexible film in the form of a mask, said film having a Young's modulus of less than 7 MPa and having a water activity of less than 0.6 in order to cosmetically treat the skin, including one or more of the following: moisturizing the skin, improving the radiance of the skin complexion, and/or smoothing the skin, and
   b) removing said film from the facial and/or body skin after step a) is completed;
   wherein said film comprises:
      at least one mineral filler representing 5 to 75 wt. % of the dry film, and
      at least one polymer of natural origin representing 15 to 75 wt. % of the dry film,
      at least one plasticizer representing 20 to 80 wt. % of the dry film,
      at least one surfactant representing 0.1 to 10 wt. % of the dry film; and
   wherein a weight ratio of said mineral filler to said polymer is equal or less than one.

2. The method of claim 1 wherein the method characterized in that the cosmetic treatment is an anti-sebum treatment, an anti-wrinkle treatment, an anti-aging treatment, a depigmenting treatment, an anti-dark circles treatment, a treatment against under-eye puffiness, and/or a treatment against skin imperfections.

3. The method of claim 1 wherein the method characterized in that the cosmetic treatment is a soothing treatment.

4. The method of claim 1, wherein the method characterized in that the cosmetic treatment is an anti-cellulite treatment.

5. The method of claim 1, wherein the dry and soluble film is characterized in that the mineral filler is selected from kaolin, talc, sodium or calcium montmorillonite, mica, illite, perlite, diatom, potassium salts, sodium salts or calcium salts, and mixtures thereof.

6. The method of claim 1 wherein the dry and soluble film is characterized in that the polymer of natural origin is selected from polymers extracted from plants or algae or microorganisms.

7. The method of claim 1, wherein the dry and soluble film is characterized in that the polymer of natural origin is a polysaccharide.

8. The method of claim 1, wherein the dry and soluble film is characterized in that the polymer of natural origin is selected from pullulan, cellulose, chitosan, acacia gum, guar gum, tara gum, gellan gum, konjac gum, xanthan gum, pectin, maltodextrin, cyclodextrins, polysaccharides, carrageenans, and mixtures thereof.

9. The method of claim 1, wherein the dry and soluble film is characterized in that it comprises at least one plasticizing agent selected from urea, glycerol, glycerol esters, glycerol ethers, monosaccharides, sorbitol, sucrose, amino acids, glycols, butylene glycol, propylene glycol, fatty alcohols, salts, lactate esters, lactate ethers, or any mixtures thereof.

10. The method of claim 1, wherein the dry and soluble film is characterized in that it also comprises at least one cosmetic active ingredient.

11. The method of claim 10, wherein the dry and soluble film is characterized in that it comprises from 0.5 to 25 wt. % of at least one cosmetic active ingredient.

12. The method of claim 10, wherein the dry and soluble film is characterized in that it comprises at least one active ingredient selected from cosmetic active ingredients which moisturize and/or smooth and/or improve the radiance of the complexion and/or have an anti-sebum and/or anti-wrinkle and/or anti-aging and/or depigmenting and/or anti-dark circles and/or anti-under-eye puffiness and/or anti-skin imperfections and/or soothing and/or anti-cellulite effect.

13. The method of claim 10, wherein the dry and soluble film promotes the transdermal penetration of the cosmetic active ingredient(s) present in the dry film.

14. The method of claim 1, wherein said film has one or more of following effects on the skin being cosmetically treated in step a): an anti-sebum, anti-wrinkle, anti-aging, depigmenting, anti-dark circles, anti-under-eye puffiness, anti-skin imperfections, soothing and/or anti-cellulite effect.

15. The method of claim 1, wherein step a) is performed for 10 to 30 minutes.

16. The method of claim 1, wherein steps a) and b) are repeated in sequence at least twice a week.

17. The method of claim 1, wherein the weight ratio of said mineral filler to said polymer of natural origin is in the range from 1:1 to 1:2 by weight, respectively.

* * * * *